(12) United States Patent
Grip

(10) Patent No.: US 8,596,997 B2
(45) Date of Patent: Dec. 3, 2013

(54) MEMBRANE PUMP WITH MAGNETIC COUPLING BETWEEN AN ACTUATING MEANS AND THE MEMBRANE

(75) Inventor: Jonathan Grip, Härnösand (SE)

(73) Assignee: Xavitech AB, Härnösand (SE)

( * ) Notice: Subject to any disclaimer, the term of this patent is extended or adjusted under 35 U.S.C. 154(b) by 0 days.

(21) Appl. No.: 13/319,400

(22) PCT Filed: May 8, 2009

(86) PCT No.: PCT/SE2009/050514
§ 371 (c)(1),
(2), (4) Date: Nov. 8, 2011

(87) PCT Pub. No.: WO2010/128914
PCT Pub. Date: Nov. 11, 2010

(65) Prior Publication Data
US 2012/0051956 A1 Mar. 1, 2012

(51) Int. Cl.
*F04B 43/04* (2006.01)
*F04B 53/22* (2006.01)

(52) U.S. Cl.
USPC .................................. 417/413.1; 417/360

(58) Field of Classification Search
USPC .......... 417/413.1, 360, 395, 420; 403/DIG. 1; 604/6.11
See application file for complete search history.

(56) References Cited

U.S. PATENT DOCUMENTS 461,375 A * 10/1891 Spaunhorst ............... 312/330.1
3,150,725 A * 9/1964 Hornschuch et al. ........... 173/93
3,515,966 A * 6/1970 Lavet et al. ................... 318/127
4,116,512 A * 9/1978 Wiser ......................... 312/330.1
4,181,477 A * 1/1980 Litt .............................. 417/560
4,614,481 A * 9/1986 Vanderjagt ................... 417/270

(Continued)

FOREIGN PATENT DOCUMENTS

EP  293241    11/1988
EP  333305     7/1993

(Continued)

OTHER PUBLICATIONS

Jezek, Types of Magnets, www.howmagnetswork.com/types.html, 2006.*

*Primary Examiner* — Devon C Kramer
*Assistant Examiner* — Nathan Zollinger
(74) *Attorney, Agent, or Firm* — Dilworth & Barrese, LLP.

(57) ABSTRACT

A membrane pump (1) has a pump housing, a membrane (4), which is mounted to the pump housing and delimits a pump chamber (8) inside the pump housing, an inlet (5) and an outlet (6) for feeding medium into and out from the pump chamber, and an actuating member (7) for moving the membrane back and forth between a first and a second position. The membrane, the inlet and the outlet are arranged in a first part (2) of the pump housing, the first part being detachably connected to a second part (3) of the pump housing, in which the actuating member is arranged. The membrane is detachably connected to the actuating member by a magnetic coupling, which has a first magnetic coupling part (9) fixed to the membrane and a corresponding second magnetic coupling part (10) fixed to the actuating member.

20 Claims, 3 Drawing Sheets

(56) References Cited

U.S. PATENT DOCUMENTS

| | | | |
|---|---|---|---|
| 4,832,582 A * | 5/1989 | Buffet | 417/413.1 |
| 5,252,044 A | 10/1993 | Raines et al. | |
| 5,816,779 A | 10/1998 | Lawless et al. | |
| 6,732,646 B2 * | 5/2004 | Zink | 101/366 |
| 2003/0004492 A1* | 1/2003 | Munis et al. | 604/503 |
| 2010/0062922 A1* | 3/2010 | Hoffmann | 494/12 |
| 2010/0135109 A1* | 6/2010 | Drees | 366/274 |

FOREIGN PATENT DOCUMENTS

| | | | | |
|---|---|---|---|---|
| EP | 398583 | 4/1994 | | |
| WO | 95/27852 | 10/1995 | | |
| WO | WO 9527852 A1 * | 10/1995 | | F04B 43/02 |
| WO | 2007/055642 | 5/2007 | | |
| WO | WO 2007055642 A1 * | 5/2007 | | H02K 33/02 |

\* cited by examiner

MEMBRANE PUMP WITH MAGNETIC COUPLING BETWEEN AN ACTUATING MEANS AND THE MEMBRANE

FIELD OF THE INVENTION AND PRIOR ART

The invention relates to a membrane pump according to the description herein.

Pumps that are used for driving a fluid in a circuit are found in a large variety of forms and sizes and are used in many different applications, from large industry pumps to small pumps for medical purposes. In some application it is desired to keep the circuit strictly clean during pumping, which may imply that parts that are in contact with the fluid to be pumped have to be replaceable and/or cleanable.

In medical applications it is usually very important that all parts of the apparatus that are in contact with the fluid to be pumped are kept in a sterilized condition. Pumps are usually expensive parts and costly to exchange, and nowadays this is solved by providing the apparatus with a peristaltic pump, provided with a gear, which never is in direct contact with the fluid. Instead, the gear of the peristaltic pump engages and compresses a plastic tube which leads the fluid in a driving direction. The gear rotates while the cogs of the gear are sliding along said tube in the driving direction. Portions of the fluid in the tube are thereby transported by the sliding cogs in said direction. When parts of the apparatus that are in contact with the fluid the only thing that needs to be exchanged is the plastic tube. Since the peristaltic pump works by sliding the cogs of its gear along a plastic tube the friction created between the plastic tube and the cogs demands a relatively strong motor of the peristaltic pump, which of course means that the peristaltic pump has relatively high energy consumption. Peristaltic pumps are used for numerous medical applications and the high energy consumption may be acceptable on large apparatuses in for instance hospitals, but for portable systems there is a need to significantly lower the energy consumption.

In some medical applications fluids are driven in circuits by membrane pumps. A membrane pump is relatively expensive so it is desirable to provide an arrangement in which only the parts of the membrane pump that have been in contact with the fluid are exchanged.

EP 0333305 A2 discloses a membrane pump which is provided with an exchangeable pump chamber in the form of a cassette. An actuator is used for driving the membrane back and forth and the cassette is screwed onto a threaded part of the actuator.

EP 0398583 A2 discloses a membrane pump which is provided with an exchangeable pump chamber. The membrane comprises piezoelectric driving means which also are exchanged when the pump chamber is exchanged.

U.S. Pat. No. 5,816,779 A discloses a disposable pumping cassette, which has a membrane to be actuated by an actuator. The actuator abuts the membrane and is arranged for compressing a pump chamber by pressing said membrane in one direction. The decompression of the pump chamber is accomplished by the intrinsic flexibility of the membrane, which causes the membrane to return to its initial position which restores the pump chamber into its decompressed state.

SUMMARY OF THE INVENTION

The object of the present invention is to provide a new and favourable membrane pump with an exchangeable pump chamber.

This object is according to the invention achieved by means of a membrane pump having the features defined herein, wherein the membrane pump comprises a pump housing, a membrane, which is mounted to the pump housing and delimits a pump chamber inside the pump housing, an inlet for feeding medium into the pump chamber, the inlet having a first non-return valve connected thereto, an outlet for discharging medium from the pump chamber, the outlet having a second non-return valve connected thereto, and actuating means for moving the membrane back and forth between a first position and a second position. The membrane, the inlet and the outlet are arranged in a first part of the pump housing, the first part being detachably connected to a second part of the pump housing, in which the actuating means is arranged. The membrane is detachably connected to the actuating means by means of a magnetic coupling, which comprises a first magnetic coupling part fixed to the membrane and a corresponding second magnetic coupling part fixed to the actuating means.

When using the membrane pump of the invention for pumping a medium, all the parts that are in contact with the medium are arranged in the first part of the pump housing. The first part is detachable from the second part which allows the first part to be exchanged if necessary. During pumping, the membrane needs to be actuated by the actuating means in order to oscillate and thereby provide the pumping force. In the inventive membrane pump the membrane is firmly connected to the actuating means by a magnetic coupling, and this allows for the first part of the pump housing to be swiftly exchanged by detaching it from the second part of the pump housing. The membranes of small membrane pumps are usually made of relatively soft materials, such as polymers, and if the membrane of a small membrane pump is connected to the actuating means by a screwed coupling as disclosed in EP 0333305 A2, the screwing could damage the membrane or twist it into an unwanted shape. The magnetic coupling in the inventive membrane pump provides a firm connection between the membrane and the actuator without the need of screwing any part onto another part, which ensures that the membrane is kept intact after mounting the first part of the pump housing to the second part of the pump housing. During pumping with a membrane pump, for instance for driving a fluid in a circuit, it is important that significant driving forces can be applied by the actuating means to the membrane in both the first and the second direction. When using a membrane pump as disclosed in U.S. Pat. No. 5,816,779 A the driving force is only applied in one direction, which significantly impair the pumping ability of the membrane pump.

According to one embodiment of the invention one of the first and the second magnetic coupling parts comprises a permanent magnet and the other magnetic coupling part comprises a ferromagnetic material. A permanent magnet attracts a ferromagnetic material which ensures that the magnetic coupling provides a firm connection between the membrane and the actuating means.

According to another embodiment of the invention the first magnetic coupling part comprises a ferromagnetic material and the second magnetic coupling part comprises a permanent magnet. A permanent magnet is usually more expensive than a ferromagnetic material and since the first part of the pump housing is the part of the pump housing to be exchanged it is advantageous if the first magnetic coupling part comprises the inexpensive ferromagnetic material and the second magnetic coupling part, which is not to be exchanged, comprises the more expensive permanent magnet.

According to another embodiment of the invention one of the first and second magnetic coupling parts comprises a protrusion configured for insertion into a corresponding recess comprised in the other magnetic coupling part. If the magnetic coupling comprises a protrusion and a corresponding recess, movements of the first and second coupling parts in relation to each other are significantly suppressed when they are connected to each other.

According to another embodiment of the invention the actuating means comprises a shaft, which at one end is provided with said second magnetic coupling part. The actuating means is driven for instance by a spring and an electromagnet or by two electromagnets and it is advantageous to have a part of the actuating means comprising a shaft affected by said spring and/or electromagnet/electromagnets. The shaft preferably moves back and forth in its longitudinal direction during pumping and is at one end connected to the membrane by said magnetic coupling. When the shaft moves, the membrane moves in the same direction as the shaft.

According to another embodiment of the invention the first part of the pump housing comprises guiding means configured for radially guiding the shaft so as to guide said protrusion into said recess. The guiding means can for instance comprise an annular opening configured for receiving the shaft of the actuating means when the first part of the pump housing is connected to the second part of the pump housing. The guiding means facilitates a correct connection of the membrane to the actuating means. This is important since pumping with the inventive pump is dependent upon a firm connection between the membrane and the actuating means. If the membrane is incorrectly connected to the actuating means there is a risk for interruption in the service during pumping.

According to another embodiment of the invention the second part of the pump housing comprises guiding means configured for restricting radial movement of the shaft in said second part of the pump housing. Radial movement of the shaft in the second part of the pump housing may damage said shaft.

According to another embodiment of the invention the first part of the pump housing is detachably connected to the second part of the pump housing by means of a coupling, which comprises a first coupling part fixed to the first part of the pump housing and a second coupling part fixed to the second part of the pump housing.

According to another embodiment of the invention the coupling of the pump housing is a snap coupling. A snap coupling provides a quick and reliable connection between the first part and the second part of the pump housing.

According to another embodiment of the invention the coupling of the pump housing is a magnetic coupling. A magnetic coupling provides a quick and reliable connection between the first part and the second part of the pump housing and it does not deteriorate over time.

According to another embodiment of the invention one of the first and second coupling parts comprises a permanent magnet and the other coupling part comprising a ferromagnetic material. A permanent magnet attracts a ferromagnetic material which ensures that the magnetic coupling provides a firm connection between the first part and the second part of the pump housing. The magnetic coupling can of course instead comprise two permanent magnets, one permanent magnet comprised in the first part and one in the other part.

According to another embodiment of the invention the first coupling part comprises a ferromagnetic material and the second coupling part comprises a permanent magnet. A permanent magnet is usually more expensive than a ferromagnetic material and since the first part of the pump housing is the part of the pump housing to be exchanged it is advantageous if the first part of the pump housing comprises the inexpensive ferromagnetic material and the second part of the pump housing, which is not to be exchanged, comprises the more expensive permanent magnet.

Other advantages and advantageous features of the invention will appear from the subsequent description.

BRIEF DESCRIPTION OF THE DRAWINGS

With reference to the appended drawings, below follows a specific description of embodiments of the invention cited as examples.

In the drawings.

DETAILED DESCRIPTION OF PREFERRED EMBODIMENTS OF THE INVENTION

Explained herein are preferred embodiments of the invention, describing the membrane pump of the invention. The invention may, however, be embodied in many different forms and should not be construed as being limited to the exemplary embodiments set forth herein; rather, these embodiments are provided so that this disclosure will be thorough and complete, and will fully convey the concept of the invention to those skilled in the art.

Figure 1:
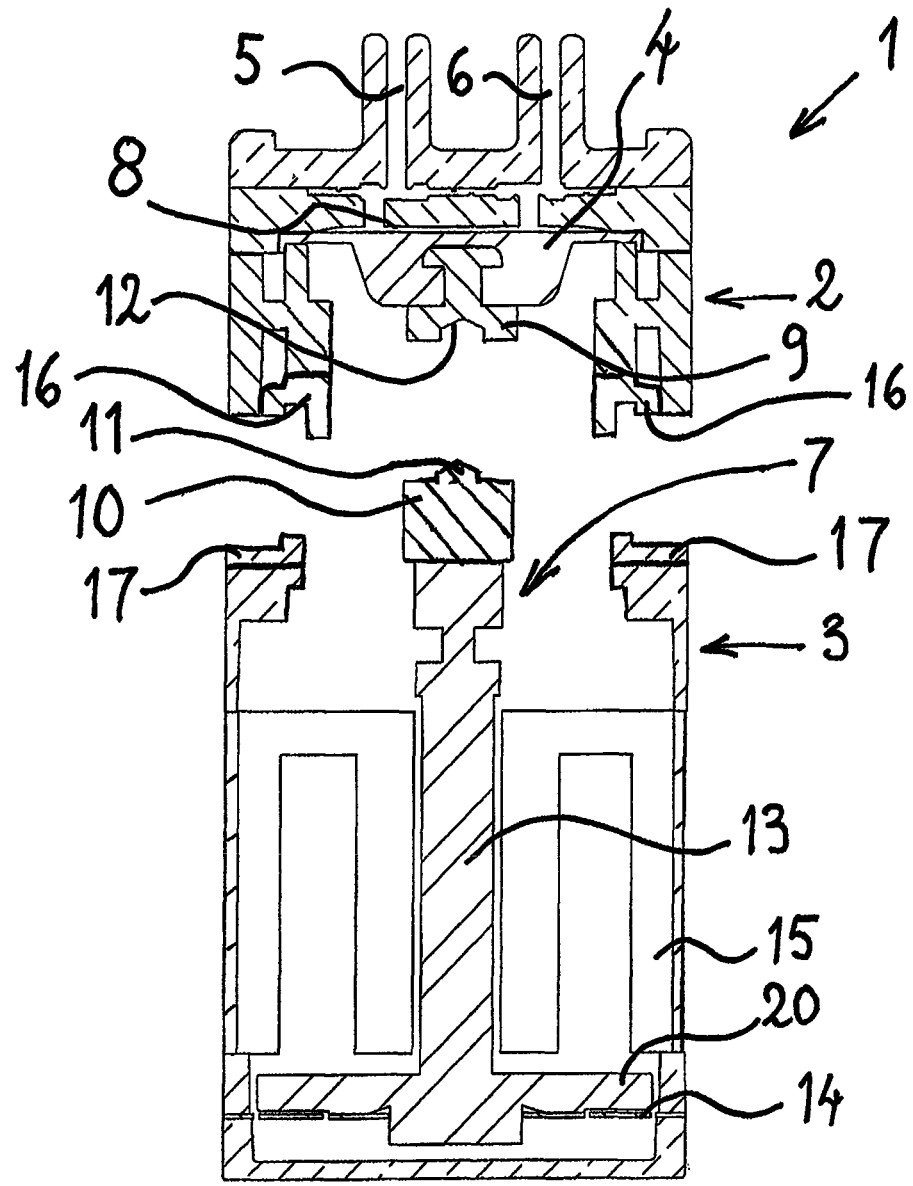
FIG. 1 shows a membrane pump according to an embodiment of the invention with a first part of the pump housing separated from a second part of the pump housing.
Figure 2:
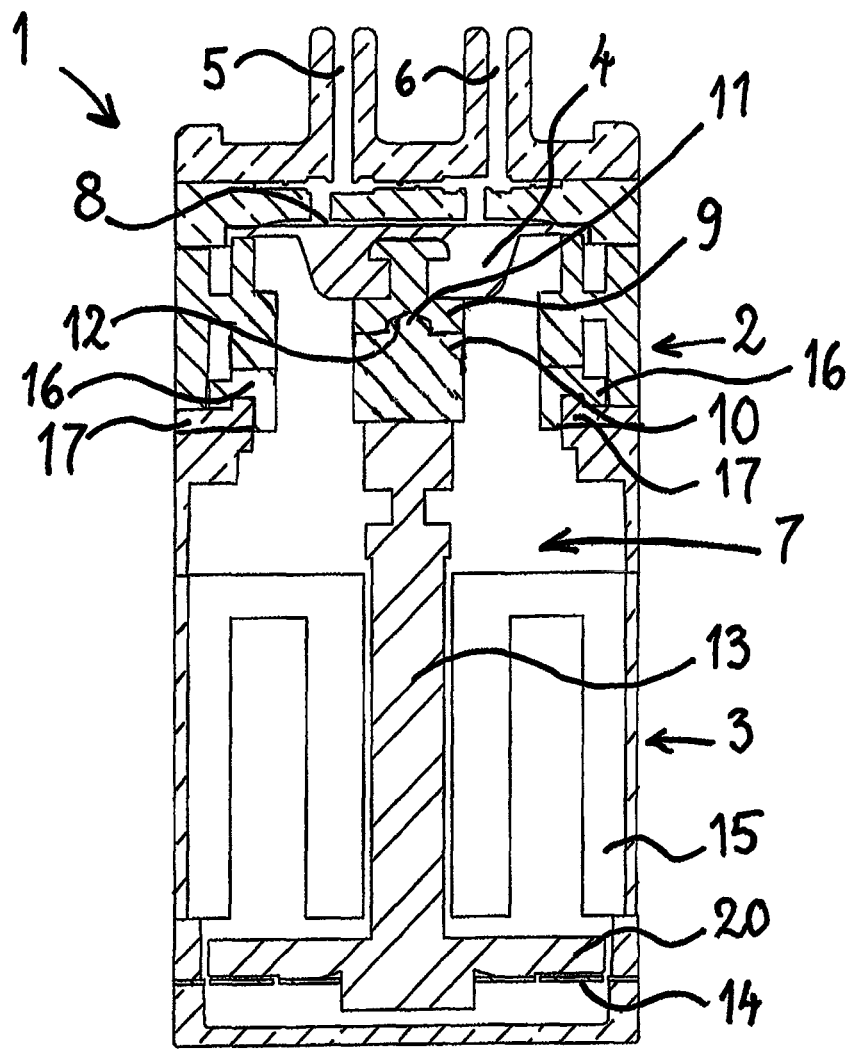
FIG. 2 shows the membrane pump of FIG. 1 with the two parts of the pump housing connected to each other.

A membrane pump 1 according to the invention is shown in FIGS. 1 and 2. In FIG. 1 the membrane pump 1 is separated into two parts 2, 3 and in FIG. 2 the membrane pump is shown in its assembled form in which the two separated parts shown in FIG. 1 are assembled. The membrane pump 1 comprises a pump housing which comprises two parts 2, 3, a first part 2 in which a membrane 4, an inlet 5 and an outlet 6 are arranged and a second part 3 in which actuating means 7 is arranged. The membrane 4 is mounted to the first part 2 of the pump housing and delimits a pump chamber 8 inside said first part 2. The inlet 5, which has a first non-return valve (not shown) connected thereto, is arranged for feeding medium into the pump chamber 8, and the outlet 6, which has a second non-return valve (not shown) connected thereto, is arranged for discharging medium from the pump chamber 8. The actuating means 7 is configured for moving the membrane 4 back and forth between a first and a second position when the membrane pump 1 is in its assembled form and in use. The membrane 4 is configured to be detachably connected to the actuating means 7 by means of a magnetic coupling, which comprises a first magnetic coupling part 9 fixed to the membrane 4 and a corresponding second magnetic coupling part 10 fixed to the actuating means 7. The magnetic coupling can be achieved by having one of the first 9 and the second 10 magnetic coupling parts comprising a permanent magnet and the other magnetic coupling part comprising a ferromagnetic material. The magnetic coupling can of course instead comprise two permanent magnets, one permanent magnet comprised in the first magnetic coupling part 9 and one in the second magnetic coupling part 10. An electromagnetic coupling is of course also possible. Preferably, the first magnetic coupling part 9 comprises a ferromagnetic material and the second magnetic coupling part 10 comprises a permanent magnet. The second magnetic coupling part 10 also comprises a protrusion 11 configured for insertion into a corresponding recess 12 comprised in the first magnetic coupling part 9. Of course a protrusion instead can be comprised in the first magnetic coupling part 9 for insertion into a corresponding recess comprised in the second magnetic coupling part 10. The actuating means 7 comprises a shaft 13, which at one end is provided with said second magnetic coupling part 10. To move the membrane 4 back and forth the shaft 13 of the actuating means 7 is driven by a spring, preferably a flat spring 14, longitudinally in one direction and an electromagnet 15 longitudinally in the opposite direction. The spring 13 can of course be replaced by a second electromagnet.

The first part 2 of the pump housing is detachably connected to the second part 3 of the pump housing by means of a coupling, which coupling comprises a first coupling part 16 fixed to the first part 2 of the pump housing and a second coupling part 17 fixed to the second part 3 of the pump housing. The coupling of the pump housing shown in FIGS. 1 and 2 is a magnetic coupling, wherein one of the first 16 and second 17 coupling parts comprises a permanent magnet and the other coupling part comprises a ferromagnetic material. The magnetic coupling can of course instead comprise two permanent magnets, one permanent magnet comprised in the first coupling part 16 and one in the second coupling part 17. Preferably the first coupling part 16 comprises a ferromagnetic material and the second coupling part 17 comprises a permanent magnet. The coupling of the pump housing can also be a snap coupling or any other coupling suitable for the purpose of connecting the first 2 and the second 3 parts of the pump housing to each other.

The first part 2 of the pump housing is exchangeable and in order to detach it from the second part 3 of the pump housing said first part 2 is moved in the longitudinal direction of said shaft 13 away from the second part 3 of the pump housing, whereby the first magnetic coupling part 9 is detached from the second magnetic coupling part 10 and the first coupling part 16 of the pump housing is detached from the second coupling part 17 of the pump housing. If the coupling of the pump housing is a snap coupling or any other coupling, other operations may be needed for detaching the first part 2 of the pump housing from the second part 3 of the pump housing. To attach the first part 2 of the pump housing to the second part 3 of the pump housing the two parts 2, 3 of the pump housing are moved towards each other so as to allow the corresponding coupling parts to come into engagement with each other.

Figure 3:
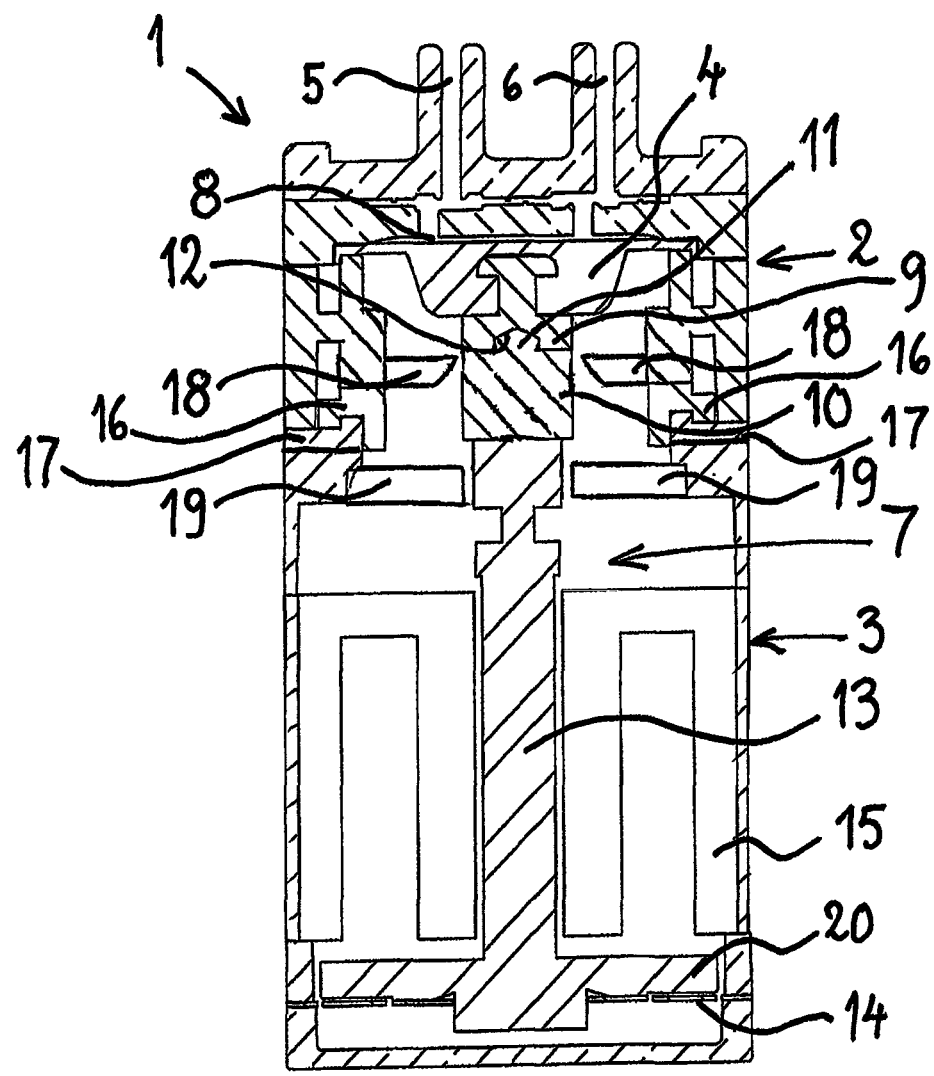
FIG. 3 shows a membrane pump according to another embodiment of the invention

In FIG. 3 it is shown a membrane pump 1 according to another embodiment of the invention. The membrane pump 1 shown in FIG. 1 resembles the membrane pumps shown in FIG. 2 and FIG. 3 but here the first part 2 of the pump housing comprises guiding means 18 configured for radially guiding the shaft 13 of the actuating means 7 so as to guide the protrusion 11 of the second magnetic coupling part 10 into the recess 12 of the first magnetic coupling part 9 when the first part 2 of the pump housing is connected to the second part 3 of the pump housing. The guiding means 18 of the first part 2 of the pump housing has a central opening configured for receiving said shaft 13 and/or the second magnetic coupling part 10. The second part 3 of the pump housing comprises guiding means 19 configured for restricting radial movement of the shaft 13 in said second part 3 of the pump housing. The guiding means 19 of the second part 3 of the pump housing is especially important when the first part 2 of the pump housing is detached, due to the risk for damaging the shaft 13 by having it hit the electromagnet 15 if said guiding means 19 is absent. The guiding means 19 of the second part 3 of the pump housing has a central opening configured for receiving said shaft 13.

During pumping using the membrane pumps 1 shown in FIGS. 1-3, in a first phase the flat spring 14 affects the shaft 13, and thereby the membrane 4, with a force pulling the membrane 4 in a direction away from the pump chamber 8, whereby the volume of the pump chamber 8 expands and the first non-return valve is opened so as to allow medium to flow into the pump chamber 8 through the inlet 5. During this first phase, the membrane 4 is moved under the action of the spring 14 from a first end position to a second end position. In a second phase the electromagnet 15 is activated, whereby the electromagnet 15 attracts a protruding magnetic part 20 of the shaft 13 and the shaft 13 is pulled in a direction towards the pump chamber 8, and the membrane 4 consequently also moves towards the pump chamber 8. The pump chamber 8 is thereby contracted and the medium flows out from the pump chamber 8 through the second non-return valve and the outlet 6. During this second phase, the membrane 4 is moved under the action of the electromagnet 15 and against the action of the spring 14 from the second end position to the first end position. Of course another electromagnet can replace the spring 14 and provide the force for pulling the membrane 4 away from the pump chamber 8. If the spring 14 is replaced by an electromagnet, the other electromagnet 15 can be replaced by another spring, which provides the force for pushing the membrane 4 towards the pump chamber 8.

The invention is of course not in any way limited to the embodiments described above. On the contrary, several possibilities to modifications thereof should be apparent to a person skilled in the art without departing from the basic idea of the invention as defined in the appended claims.

The invention claimed is:

1. A membrane pump (1) comprising:
   a pump housing,
   a membrane (4), which is mounted to the pump housing and delimits a pump chamber (8) inside the pump housing,
   an inlet (5) for feeding medium into the pump chamber (8), the inlet (5) having a first non-return valve connected thereto,
   an outlet (6) for discharging medium from the pump chamber (8), the outlet (6) having a second non-return valve connected thereto, and
   actuating means (7) for moving the membrane (4) back and forth between a first and a second position in an axial direction, wherein
   the membrane (4), the inlet (5) and the outlet (6) are arranged in a first exchangeable part (2) of the pump housing, the first exchangeable part (2) being detachably connected in the axial direction to a second part (3) of the pump housing, in which the actuating means (7) is arranged to form an integral structure encompassing both the membrane (4) and actuating means (7),
   the membrane (4) is detachably connected to the actuating means (7) by a magnetic coupling, which comprises a first magnetic coupling part (9) fixed to the membrane (4) and a corresponding second magnetic coupling part (10) fixed to the actuating means (7), and
   said first and second magnetic coupling parts (9, 10) are detachably fixed to one another to directly contact one another.

2. A membrane pump (1) according to claim 1, wherein one of the first (9) and the second (10) magnetic coupling parts comprises a permanent magnet and the other magnetic coupling part comprises a ferromagnetic material.

3. A membrane pump (1) according to claim 2, wherein the first magnetic coupling part (9) comprises a ferromagnetic material and that the second magnetic coupling part (10) comprises a permanent magnet.

4. A membrane pump (1) according to claim 1, wherein one of the first (9) and second (10) magnetic coupling parts comprises a protrusion (11) configured for insertion into a corresponding recess (12) comprised in the other magnetic coupling part, and with said first and second magnetic coupling parts (9, 10) axially-fixable to one another and axially-movable as a unit.

5. A membrane pump (1) according to claim 4, wherein the second magnetic coupling part (10) comprises said protrusion (11) configured for insertion into said corresponding recess (12) comprised in the first magnetic coupling part (9).

6. A membrane pump (1) according to claim 1, wherein the actuating means (7) comprises a shaft (13), which at one end is provided with said second magnetic coupling part (10).

7. A membrane pump (1) according to claim 6 wherein one of the first (9) and second (10) magnetic coupling parts comprises a protrusion (11) configured for insertion into a corresponding recess (12) comprised in the other magnetic coupling part, and the first part (2) of the pump housing comprises guiding means (18) configured as a narrowing of a central opening inside the first part (2) of the pump housing for radially guiding the shaft (13) to guide said protrusion (11) into said recess (12) when the first part (2) of the pump housing is connected to the second part (3) of the pump housing.

8. A membrane pump (1) according to claim 6, wherein the second part (3) of the pump housing comprises guiding means (19) configured as a narrowing of an opening out of the second part (3) of the pump housing and through which the shaft (13) protrudes for restricting radial movement of the shaft (13) in said second part (3) of the pump housing.

9. A membrane pump (1) according to claim 1, wherein the first part (2) of the pump housing is detachably connected to the second part (3) of the pump housing by a coupling, which comprises a first coupling part (16) fixed to the first part (2) of the pump housing and a second coupling part (17) fixed to the second part (3) of the pump housing, said first and second coupling parts (16, 17) of the pump housing circumferentially positioned around and spaced from said respective magnetic coupling parts (9, 10).

10. A membrane pump (1) according to claim 9, wherein the first and second coupling parts (16, 17) of the pump housing are configured to snap into engagement with each other.

11. A membrane pump (1) according to claim 9, wherein the coupling of the pump housing is a magnetic coupling.

12. A membrane pump (1) according to claim 11, wherein one of the first (16) and second (17) coupling parts comprises a permanent magnet and the other coupling part comprises a ferromagnetic material.

13. A membrane pump (1) according to claim 12, wherein the first coupling part (16) comprises a ferromagnetic
material and the second coupling part (17) comprises a permanent magnet.

14. A membrane pump (1) according to claim 1, wherein the first magnetic coupling part (9) is directly fixed to the membrane (4).

15. A membrane pump (1) according to claim 1, wherein the inlet (5) and outlet (6) are parallel and laterally disposed to one another and parallel to direction of oscillation of the membrane (7).

16. A membrane pump (1) according to claim 6, wherein said shaft (13) has a radially-protruding part (20) at an end opposite said second magnetic coupling part (10).

17. A membrane pump (1) according to claim 16, additionally comprising a flat spring (14) adjacent said radially-protruding part (20) and on a side thereof opposite said second magnetic coupling part (10) to pull the membrane (4) away from the pump chamber (8).

18. A membrane pump (1) according to claim 4, wherein said first magnetic coupling part (9) comprises said recess (11) and a plug on an opposite end from said recess (11) and affixed to said membrane (4) and said second magnetic coupling part (10) comprises said protrusion (11) mounted at an end of an axially-movable shaft (13).

19. A membrane pump (1) according to claim 1, wherein when the pump housing parts (2, 3) are uncoupled, the first magnetic coupling part (9) is recessed within the first exchangeable part (2) of the pump housing and the second magnetic coupling part (10) protrudes out from the second part (3) of the pump housing.

20. A membrane pump (1) according to claim 1, wherein the first and second parts (2, 3) of the pump housing are circumferentially seated around both the membrane (4) and actuating means (7) when coupled together.

* * * * *